(12) United States Patent
Cheng et al.

(10) Patent No.: US 10,960,640 B2
(45) Date of Patent: *Mar. 30, 2021

(54) MULTI-LAYERED ELASTIC AIR-PERMEABLE MATERIAL STRUCTURE

(71) Applicant: GOLDEN PHOENIX FIBERWEBS, INC., Tainan (TW)

(72) Inventors: Kenneth Cheng, Taipei (TW); Eric Shyuu, Taipei (TW)

(73) Assignee: GOLDEN PHOENIX FIBERWEBS, INC., Tainan (TW)

(*) Notice: Subject to any disclaimer, the term of this patent is extended or adjusted under 35 U.S.C. 154(b) by 0 days.

This patent is subject to a terminal disclaimer.

(21) Appl. No.: 16/638,236

(22) PCT Filed: Jan. 29, 2019

(86) PCT No.: PCT/CN2019/073651
§ 371 (c)(1),
(2) Date: Feb. 11, 2020

(87) PCT Pub. No.: WO2019/223360
PCT Pub. Date: Nov. 28, 2019

(65) Prior Publication Data
US 2020/0198284 A1 Jun. 25, 2020

(30) Foreign Application Priority Data
May 25, 2018 (CN) .......................... 201810516114.X

(51) Int. Cl.
*B32B 27/12* (2006.01)
*B32B 3/26* (2006.01)
(Continued)

(52) U.S. Cl.
CPC .............. *B32B 3/266* (2013.01); *B32B 5/022* (2013.01); *B32B 7/12* (2013.01); *B32B 25/10* (2013.01);
(Continued)

(58) Field of Classification Search
CPC ........... A41B 17/00; A61F 13/51; B32B 1/00; B32B 2262/0215; B32B 2262/0276;
(Continued)

(56) References Cited

FOREIGN PATENT DOCUMENTS

| CN | 204773829 U | 11/2015 |
|---|---|---|
| CN | 105232230 A | 1/2016 |

(Continued)

*Primary Examiner* — Lawrence D Ferguson
(74) *Attorney, Agent, or Firm* — WPAT, PC

(57) ABSTRACT

The present invention relates to a multi-layered elastic air-permeable material structure, including an elastic cloth and an elastic film, wherein the elastic cloth is constituted of polylactic acid, has a plurality of penetrating air vents, and has a weft-direction stretchability. The elastic film is constituted of a thermoplastic elastomer material, and it also has a plurality of penetrating air vents. An upper surface of the elastic film is entirely or partially adhered to a lower surface of the elastic cloth. In particular, the elastic film has an air permeability of 17-25 cc/sec per square centimeter, and the multi-layered elastic air-permeable material structure has an air permeability of 7-10 cc/sec per square centimeter. The present invention has the advantages of weft-direction stretchability and air permeability and is suitable for applying to close-fitting clothing or diapers to improve comfort and prevent sultriness and moisture.

5 Claims, 2 Drawing Sheets

(51) Int. Cl.
- *B32B 5/02* (2006.01)
- *B32B 7/12* (2006.01)
- *B32B 25/10* (2006.01)
- *B32B 27/30* (2006.01)
- *B32B 27/32* (2006.01)
- *B32B 27/34* (2006.01)
- *B32B 27/36* (2006.01)
- *B32B 27/40* (2006.01)

(52) U.S. Cl.
CPC ............ *B32B 27/12* (2013.01); *B32B 27/302* (2013.01); *B32B 27/32* (2013.01); *B32B 27/34* (2013.01); *B32B 27/36* (2013.01); *B32B 27/40* (2013.01); *B32B 2262/0215* (2013.01); *B32B 2262/0276* (2013.01); *B32B 2274/00* (2013.01); *B32B 2307/51* (2013.01); *B32B 2307/724* (2013.01)

(58) Field of Classification Search
CPC ............ B32B 2274/00; B32B 2307/51; B32B 2307/724; B32B 25/10; B32B 27/02; B32B 27/06; B32B 27/12; B32B 27/30; B32B 27/302; B32B 27/32; B32B 27/34; B32B 27/36; B32B 27/40; B32B 3/266; B32B 3/28; B32B 5/022; B32B 7/12
See application file for complete search history.

(56) References Cited

FOREIGN PATENT DOCUMENTS

| | | |
|---|---|---|
| CN | 108524104 A | 9/2018 |
| CN | 108542602 A | 9/2018 |
| CN | 208558516 U | 3/2019 |
| CN | 208558517 U | 3/2019 |

MULTI-LAYERED ELASTIC AIR-PERMEABLE MATERIAL STRUCTURE

CROSS-REFERENCE TO RELATED APPLICATION

This application claims the priority of Chinese patent application No. 201810516114.X, filed on May 25, 2018, which is incorporated herewith by reference.

BACKGROUND OF THE INVENTION

1. Field of the Invention

The present invention relates to a multi-layered elastic air-permeable material structure, more particularly, at least one polylactic acid elastic cloth with weft-direction stretchability is used to be adhered to at least one elastic film to achieve the characteristics of high air permeability and to have strong resilience in the weft direction.

2. The Prior Arts

When considering hygiene and using safety, general sanitary products, such as masks, disposable clothing, baby diapers or adult diapers, are usually provided in one-time or disposable usage manners to avoid contamination by germs or harmful substances. Since these products will be in contact with skin for a period of time, the air permeability requirements are stricter to prevent discomfort or allergy, itch, and even rash of the skin caused by sultriness or moisture.

Because the non-woven fabrics made of plastic materials have the advantages of being easy to manufacture, process, good chemical resistance, durability and low cost, they have been widely used in many sanitary products. However, the non-woven fabrics have poor stretchability, which may cause using inconvenience in applications, such as diapers, which needs to be worn. Therefore, the industry has developed a non-woven fabric capable of improving the stretchability, which can be called elastic non-woven fabric.

In related arts, generally, a unidirectional stretching force is applied to the non-woven fabric, and then the fiber structure is destroyed. After the original applied force is released, the non-woven fabric naturally recovers and contracts to form a unidirectional elastically-stretched elastic non-woven fabric.

In addition, the industry brings up a multi-layered composite structure to enhance the effect of the elastic recovering force. Usually, an elastic film is sandwiched between both elastic non-woven fabrics at upper and lower layers, thereby providing a function similar to elastic ribbons for convenient wearing. However, this related art has the disadvantage that the elastic film itself has a poor air permeability, which significantly reduces the overall air permeability and is unfavorable to the touch feel of the skin.

Therefore, there is a very need for an innovative multi-layered elastic air-permeable material structure, wherein a polylactic acid elastic cloth with weft-direction stretchability is used to be adhered to an elastic film to achieve high air permeability. And the multi-layered elastic air-permeable material structure has strong resilience in the weft direction, and it is suitable for fabricating close-fitting clothing or diapers, thereby solving all the problems of the above-mentioned related arts.

SUMMARY OF THE INVENTION

The main objective of the present invention is to provide a multi-layered elastic air-permeable material structure, comprising an elastic cloth and an elastic film; wherein the elastic cloth is constituted of polylactic acid, has a plurality of penetrating air vents, and has a stretchability of 150% to 400% in the weft direction; and the elastic film is constituted of a thermoplastic elastomer material such as TPE-E/S/A, TPO, TPV or TPU and has a plurality of penetrating air vents. An upper surface of the elastic film is entirely or partially adhered to a lower surface of the elastic cloth. Particularly, the elastic film has an air permeability of 17-25 cc/sec per square centimeter, and the multi-layered elastic air-permeable material structure has an air permeability of 7-10 cc/sec per square centimeter. Further, the air vents of the elastic film are aligned or misaligned with the air vents of the elastic cloth.

Since the elastic cloth only has stretchable resilience in the weft direction but not in the warp direction, and the elastic film can be directly or indirectly adhered to the elastic cloth, thereby providing the elastic cloth with greater weft-direction recoverability. Therefore, the entire multi-layered elastic air-permeable material structure has a highly strong recovering force with respect to the elastic-stretching in the weft direction. In addition, the elastic cloth and the elastic film have the advantage of proper air permeability, and they are quite suitable for applying in fields of close-fitting clothing or diapers to improve comfort and prevent rash or itch caused by sultriness and moisture.

Figure 1:
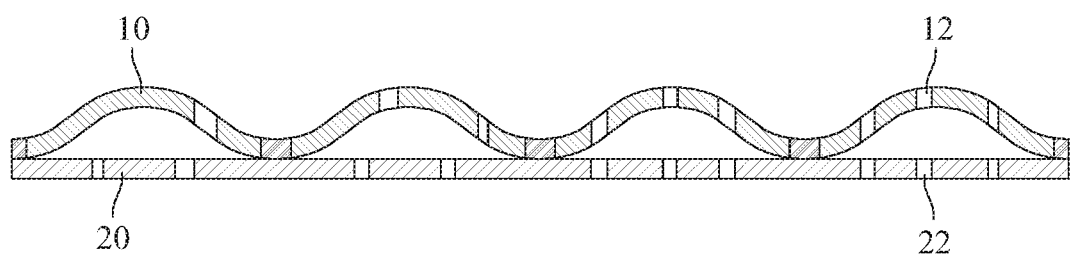
FIG. 1 is a schematic view showing a multi-layered elastic air-permeable material structure according to a first embodiment of the present invention.

Wherein, the reference numerals are described as follows:
10 elastic cloth
12 air vent
20 elastic film
22 air vent
30 another elastic cloth
32 air vent
40 another elastic film
42 air vent

DETAILED DESCRIPTION OF THE PREFERRED EMBODIMENT

Embodiments of the present invention will be described in more detail below with reference to the drawings and the reference numerals, such that those skilled in the art can implement it after studying this specification.

Refer to FIG. 1, which is a schematic view of a multi-layered elastic air-permeable material structure of a first embodiment of the present invention. As shown in FIG. 1, the multi-layered elastic air-permeable material structure of the first embodiment of the present invention comprises an elastic cloth 10 and an elastic film 20, wherein an upper surface of the elastic film 20 is entirely or partially adhered to a lower surface of the elastic cloth 10, thereby forming a double-layered stack structure. The above-mentioned partial adhering may have various implementations for achieving local dot-shaped adhering, grid-shaped adhering, stripshaped adhering and the like in matrix arrangements, while FIG. 1 shows an exemplary example of the partial adhering.

Specifically, the elastic cloth 10 is constituted of polylactic acid (PLA), may be a non-woven fabric, and has a plurality of air vents 12 penetrating an upper surface and the lower surface of the elastic cloth 10. In particular, the elastic cloth 10 has a stretchability in the weft direction, wherein the stretchability is preferably 150% to 400%.

The above-mentioned elastic film 20 is constituted of a thermoplastic elastomer material, such as a thermoplastic polyester (TPE-E), a thermoplastic polystyrenic block (TPE-S), a thermoplastic polyamide (TPE-A), a thermoplastic polyolefin (TPO), a thermoplastic vulcanizate (TPV) or a thermoplastic polyurethane (TPU), and has a plurality of air vents 22 penetrating the upper surface and an lower surface of the elastic film 20. In particular, the elastic film 20 has an air permeability of 17-25 cc/sec per square centimeter.

Further, the air vents 22 of the elastic film 20 can be aligned or misaligned with the air vents 12 of the elastic cloth 10. The entire multi-layered elastic air-permeable material structure has an air permeability which is specially designed to 7-10 cc/sec per square centimeter.

In addition, the upper surface of the elastic film 20 and the lower surface of the elastic cloth 10 can be directly adhered into a double-layered structure by ultrasonic fusion or hot-pressing fusion; or can also be adhered by coating an additional adhesive material (not shown) between the elastic film 20 and the elastic cloth 10, wherein the adhesive material can be styrene/isoprene/styrene (SIS) or styrene/ethylene-butylene/styrene (SEBS). Another way is directly extruding the adhesive material to the elastic cloth 10 to form the elastic film 20, which can achieve the adhering purpose at the same time.

More specifically, after the elastic film 20 is partially adhered to the elastic cloth 10 and then stretched in the weft direction, the permanent deformation rate of the elastic cloth 10 is higher than that of the elastic film 20; thereby after retraction, a portion not subjected to ultrasonic fusion will form wavy-shape surface bulges (as shown in the figure), which can greatly increase the surface area and expand the application field; meanwhile, the cotton feel and the thick and firm feel due to the fluffy cloth surface can be enhanced as well.

Figure 2:
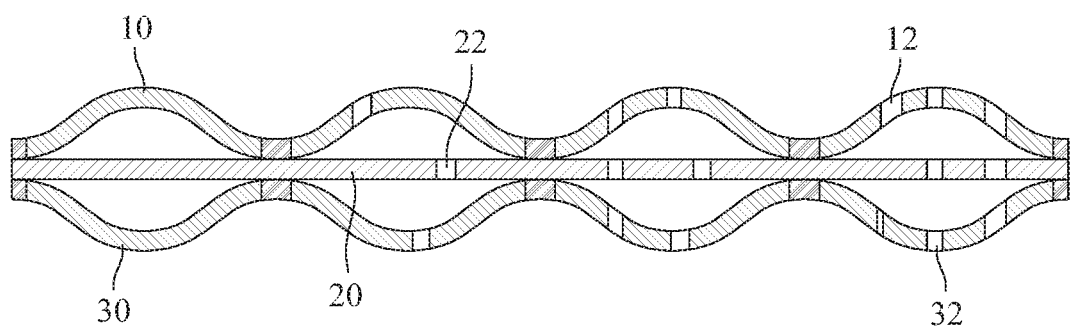
FIG. 2 is a schematic view showing a multi-layered elastic air-permeable material structure according to a second embodiment of the present invention.

Next, refer to FIG. 2, which is a schematic view of a multi-layered elastic air-permeable material structure of a second embodiment of the present invention similar to the first embodiment. The main differences thereof are that the second embodiment further comprises an another elastic cloth 30, which is also constituted of polylactic acid and has a plurality of penetrating air vents 32. An upper surface of the another elastic cloth 30 is entirely or partially adhered to the lower surface of the elastic film 20. Further, the air vents 32 of the another elastic cloth 30 are aligned or misaligned with the air vents 22 of the elastic film 20, that is, the air vents 32 are under the elastic film 20 of the first embodiment.

Figure 3:
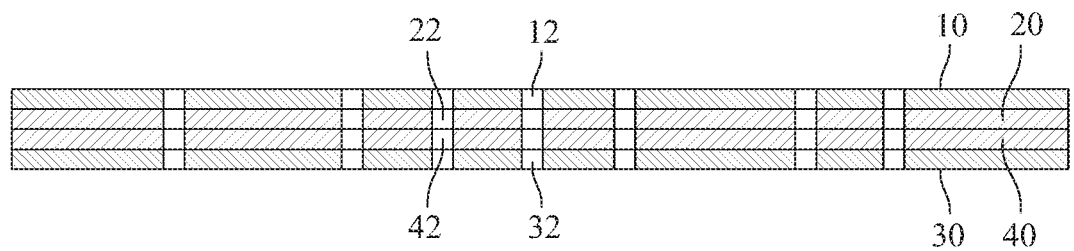
FIG. 3 is a schematic view showing a multi-layered elastic air-permeable material structure according to a third embodiment of the present invention.

FIG. 3 is a schematic view of a multi-layered elastic air-permeable material structure of a third embodiment of the present invention, which is a four-layered structure including the elastic cloth 10, the elastic film 20, the another elastic cloth 30, and an another elastic film 40, wherein the another elastic film 40 is also constituted of a thermoplastic elastomer material; and the elastic cloth 10, the elastic film 20, the another elastic film 40 and the another elastic cloth 30 are sequentially stacked from top to bottom. In addition, these layers are not fully adhered therebetween. Likewise, the another elastic film 40 has a plurality of penetrating air vents 42 that can be aligned or misaligned with the air vents 22 and the air vents 32. It should be noted that this figure shows an example that the air vents 12, the air vents 22, the air vents 42, the air vents 32 are aligned with one another.

The above-mentioned air vents 12, air vents 22, air vents 42, air vents 32 can be formed by the manners of needle piercing or needle punching. For example, by using the pin wheel, because the needle tips on the pin wheel have a high temperature, it can achieve the punching purpose and thus forms the air vents in a circular ring-shape vent arrangement, and can achieve the optimal air permeability by adjusting and changing the vent diameter or the density of arrangement. In addition, it can also be achieved by hot-pressing punching. First, the entire multi-layered elastic air-permeable material structure is rolled by a set of upper and lower pressing rollers respectively with male and female threads, and the then the punching effect is achieved by high temperature. Next, the surfaces are roll-flattened by a set of smooth-surfaced pressing rollers. Alternatively, the elastic films are processed into mesh films with vents in advance before adhered to the elastic cloths. Then the elastic films are adhered to the elastic cloths, thereby the air permeability can be improved as well.

In summary, the present invention is characterized in that the elastic cloth itself has stretchable resilience only in the weft direction, but does not have stretchable resilience in the warp direction; and the elastic film can be directly or indirectly adhered to the elastic cloth, which additionally provides the elastic cloth with greater weft-direction recoverability, thereby obtaining a multi-layered elastic air-permeable material structure with elastic-stretching in the weft direction. Particularly, the elastic cloth and the elastic film have proper air permeability, and thus are quite suitable for applying in fields of close-fitting clothing, diapers, sanitary products to improve comfort and prevent rash or itch caused by sultriness and moisture.

The mentioned above are only preferred embodiments for explaining the present invention but intend to limit the present invention in any forms, so that any modifications or verification relating to the present invention made in the same spirit of the invention should still be included in the scope of the invention as intended to be claimed.

What is claimed is:

1. A multi-layered elastic air-permeable material structure, comprising:
    an elastic cloth constituted of polylactic acid (PLA) and having a plurality of penetrating air vents; the elastic cloth has a stretchability of 150% to 400% in a weft direction; and
    an elastic film constituted of a thermoplastic elastomer material and having a plurality of penetrating air vents; an upper surface of the elastic film is entirely or partially adhered to a lower surface of the elastic cloth, and the elastic film has an air permeability of 17-25 cc/sec per square centimeter;
    wherein, the air vents of the elastic film are aligned or misaligned with the air vents of the elastic cloth; and the multi-layered elastic air-permeable material structure has an air permeability of 7-10 cc/sec per square centimeter.

2. The multi-layered elastic air-permeable material structure according to claim 1, wherein the thermoplastic elastomer material is a thermoplastic polyester (TPE-E), a thermoplastic polystyrenic block (TPE-S), a thermoplastic polyamide (TPE-A), a thermoplastic polyolefin (TPO), a thermoplastic vulcanizate (TPV) or a thermoplastic polyurethane (TPU).

3. The multi-layered elastic air-permeable material structure according to claim 1, wherein the upper surface of the elastic film and the lower surface of the elastic cloth are adhered by an adhesive material, and the adhesive material is styrene/isoprene/styrene (SIS) or styrene/ethylene-butylene/styrene (SEBS).

4. The multi-layered elastic air-permeable material structure according to claim 1, further comprising an another elastic cloth, wherein an upper surface of the another elastic cloth is entirely or partially adhered to a lower surface of the elastic film; and the another elastic cloth is constituted of polylactic acid and has a plurality of penetrating air vents aligned or misaligned with the air vents of the elastic film.

5. The multi-layered elastic air-permeable material structure according to claim 1, further comprising an another elastic cloth and an another elastic film, wherein an upper surface of the another elastic film is partially adhered to a lower surface of the elastic film, and an upper surface of the another elastic cloth is partially adhered to a lower surface of the another elastic film; the another elastic film is constituted of the thermoplastic elastomer material and has a plurality of penetrating air vents, and the another elastic cloth is constituted of polylactic acid and has a plurality of penetrating air vents; the air vents of the another elastic film are aligned or misaligned with the air vents of the elastic film, and the air vents of the another elastic cloth are aligned or misaligned with the air vents of the another elastic film.

* * * * *